(12) United States Patent
Cooper et al.

(10) Patent No.: US 8,220,468 B2
(45) Date of Patent: *Jul. 17, 2012

(54) STERILE DRAPE INTERFACE FOR ROBOTIC SURGICAL INSTRUMENT

(75) Inventors: Thomas G. Cooper, Menlo Park, CA (US); Craig R. Ramstad, Minden, NV (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/004,661

(22) Filed: Jan. 11, 2011

(65) Prior Publication Data

US 2011/0168189 A1    Jul. 14, 2011

Related U.S. Application Data

(63) Continuation of application No. 12/060,084, filed on Mar. 31, 2008, now Pat. No. 7,886,743.

(51) Int. Cl.
*A61B 19/08* (2006.01)
*A61B 1/00* (2006.01)
(52) U.S. Cl. ......... 128/852; 606/130; 600/121; 600/124
(58) Field of Classification Search .................. 128/849, 128/852; 600/118, 121–122, 124–125, 130; 606/101, 130
See application file for complete search history.

(56) References Cited

U.S. PATENT DOCUMENTS

| | | | |
|---|---|---|---|
| 4,919,112 A | 4/1990 | Siegmund | |
| 5,740,699 A | 4/1998 | Ballantyne et al. | |
| 6,346,072 B1 | 2/2002 | Cooper | |
| 6,491,701 B2 | 12/2002 | Tierney et al. | |
| 7,025,064 B2 | 4/2006 | Wang et al. | |
| 2006/0161138 A1 | 7/2006 | Orban, III et al. | |
| 2006/0199999 A1 | 9/2006 | Ikeda et al. | |
| 2008/0065105 A1 | 3/2008 | Larkin et al. | |

FOREIGN PATENT DOCUMENTS

WO    WO9832391 A1    7/1998

OTHER PUBLICATIONS

PCT/US09/38563 International Search Report and Written Opinion of the International Searching Authority, mailed Sep. 2, 2009, 10 pages.

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

*Primary Examiner* — Patricia Bianco
*Assistant Examiner* — Camtu Nguyen

(57) ABSTRACT

A robotic surgical system includes a sterile surgical instrument, a robotic surgical manipulator, and a sterile drape covering at least a portion of the robotic surgical manipulator. The surgical instrument has a proximal interface and a distal end effector. The proximal interface includes a gimbal assembly with two intersecting rotational axes coupled to the distal end effector. The robotic surgical manipulator has a drive plate that bears against the gimbal assembly. The drive plate has two degrees of rotational freedom about a center of motion that is coincident with an intersection of the axes of the gimbal assembly. The sterile drape includes a sterile sheet covers at least a portion of the robotic surgical manipulator, a frame bonded to the sterile sheet, an instrument interface that covers the drive plate of the robotic surgical manipulator, and a diaphragm that connects the instrument interface to the frame.

19 Claims, 4 Drawing Sheets

STERILE DRAPE INTERFACE FOR ROBOTIC SURGICAL INSTRUMENT

This application is a continuation of U.S. patent application Ser. No. 12/060,084 (filed Mar. 31, 2008; now U.S. Pat. No. 7,886,743 A1), which is hereby incorporated by reference in its entirety.

BACKGROUND

1. Field

Embodiments of the invention relate to the field of surgical drapes; and more specifically, to surgical drapes for robotic manipulators with provisions for transferring motion to attached surgical instruments.

2. Background

Minimally invasive medical techniques have been used to reduce the amount of extraneous tissue which may be damaged during diagnostic or surgical procedures, thereby reducing patient recovery time, discomfort, and deleterious side effects. Traditional forms of minimally invasive surgery include endoscopy. One of the more common forms of endoscopy is laparoscopy, which is minimally invasive inspection or surgery within the abdominal cavity. In traditional laparoscopic surgery, a patient's abdominal cavity is insufflated with gas and cannula sleeves are passed through small (approximately ½-inch) incisions in the musculature of the patient's abdomen to provide entry ports through which laparoscopic surgical instruments can be passed in a sealed fashion.

The laparoscopic surgical instruments generally include a laparoscope for viewing the surgical field and working tools defining end effectors. Typical surgical end effectors include clamps, graspers, scissors, staplers, and needle holders, for example. The working tools are similar to those used in conventional (open) surgery, except that the working end or end effector of each tool is separated from its handle by an approximately 12-inch long extension tube, for example, so as to permit the operator to introduce the end effector to the surgical site and to control movement of the end effector relative to the surgical site from outside a patient's body.

In order to provide improved control of the working tools, it may be desirable to control the instrument with a robotic manipulator. The surgeon may operate controls on a console to indirectly manipulate the instrument that is connected to the robotic manipulator. The instrument is detachably coupled to the robotic manipulator so that the instrument can be separately sterilized and selected for use as needed instrument for the surgical procedure to be performed. The instrument may be changed during the course of a surgery.

Performing surgery robotically creates new challenges. One such challenge results from the fact that a portion of the electromechanical robotic surgical manipulator will be in direct contact with the surgical instruments, and will also be positioned adjacent the operation site. Accordingly, the robotic manipulator may become contaminated during surgery and is typically disposed of or sterilized between operations. From a cost perspective, it would be preferable to sterilize the device. However, the servo motors, sensors, encoders and electrical connections that are necessary to robotically control the motors typically cannot be sterilized using conventional methods, e.g., steam, heat and pressure or chemicals, because they would be damaged or destroyed in the sterilization process.

Another challenge with robotic surgery systems is that a surgeon will typically employ a large number of different surgical instruments during a procedure. Since the number of instrument holders are limited due to space constraints and cost, many of these surgical instruments will be attached and detached from the same instrument holder a number of times during an operation. In laparoscopic procedures, for example, the number of entry ports into the patient's abdomen is generally limited during the operation because of space constraints as well as a desire to avoid unnecessary incisions in the patient. Thus, a number of different surgical instruments will typically be introduced through the same trocar sleeve during the operation. Likewise, in open surgery, there is typically not enough room around the surgical site to position more than one or two surgical manipulators, and so the surgeon's assistant will be compelled to frequently remove instruments from the robotic manipulator and exchange them with other surgical tools.

It would be desirable to provide a way of preventing contamination of the robotic manipulator and allowing quick and reliable attachment of a succession of surgical instruments while maintaining a sterile field.

SUMMARY

A robotic surgical system includes a sterile surgical instrument, a robotic surgical manipulator, and a sterile drape covering at least a portion of the robotic surgical manipulator. The surgical instrument has a proximal interface and a distal end effector. The proximal interface includes a gimbal assembly with two intersecting rotational axes coupled to the distal end effector. The robotic surgical manipulator has a drive plate that bears against the gimbal assembly. The drive plate has two degrees of rotational freedom about a center of motion that is coincident with an intersection of the axes of the gimbal assembly. The sterile drape includes a sterile sheet covers at least a portion of the robotic surgical manipulator, a frame bonded to the sterile sheet, an instrument interface that covers the drive plate of the robotic surgical manipulator, and a diaphragm that connects the instrument interface to the frame.

Other features and advantages of the present invention will be apparent from the accompanying drawings and from the detailed description that follows below.

BRIEF DESCRIPTION OF THE DRAWINGS

The invention may best be understood by referring to the following description and accompanying drawings that are used to illustrate embodiments of the invention by way of example and not limitation. In the drawings, in which like reference numerals indicate similar elements.

DETAILED DESCRIPTION

In the following description, numerous specific details are set forth. However, it is understood that embodiments of the invention may be practiced without these specific details. In other instances, well-known circuits, structures and techniques have not been shown in detail in order not to obscure the understanding of this description.

In the following description, reference is made to the accompanying drawings, which illustrate several embodiments of the present invention. It is understood that other embodiments may be utilized, and mechanical compositional, structural, electrical, and operational changes may be made without departing from the spirit and scope of the present disclosure. The following detailed description is not to be taken in a limiting sense, and the scope of the embodiments of the present invention is defined only by the claims of the issued patent.

The terminology used herein is for the purpose of describing particular embodiments only and is not intended to be limiting of the invention. Spatially relative terms, such as "beneath", "below", "lower", "above", "upper", and the like may be used herein for ease of description to describe one element's or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the exemplary term "below" can encompass both an orientation of above and below. The device may be otherwise oriented (e.g., rotated 90 degrees or at other orientations) and the spatially relative descriptors used herein interpreted accordingly.

As used herein, the singular forms "a", "an", and "the" are intended to include the plural forms as well, unless the context indicates otherwise. It will be further understood that the terms "comprises" and/or "comprising" specify the presence of stated features, steps, operations, elements, and/or components, but do not preclude the presence or addition of one or more other features, steps, operations, elements, components, and/or groups thereof.

Figure 1:
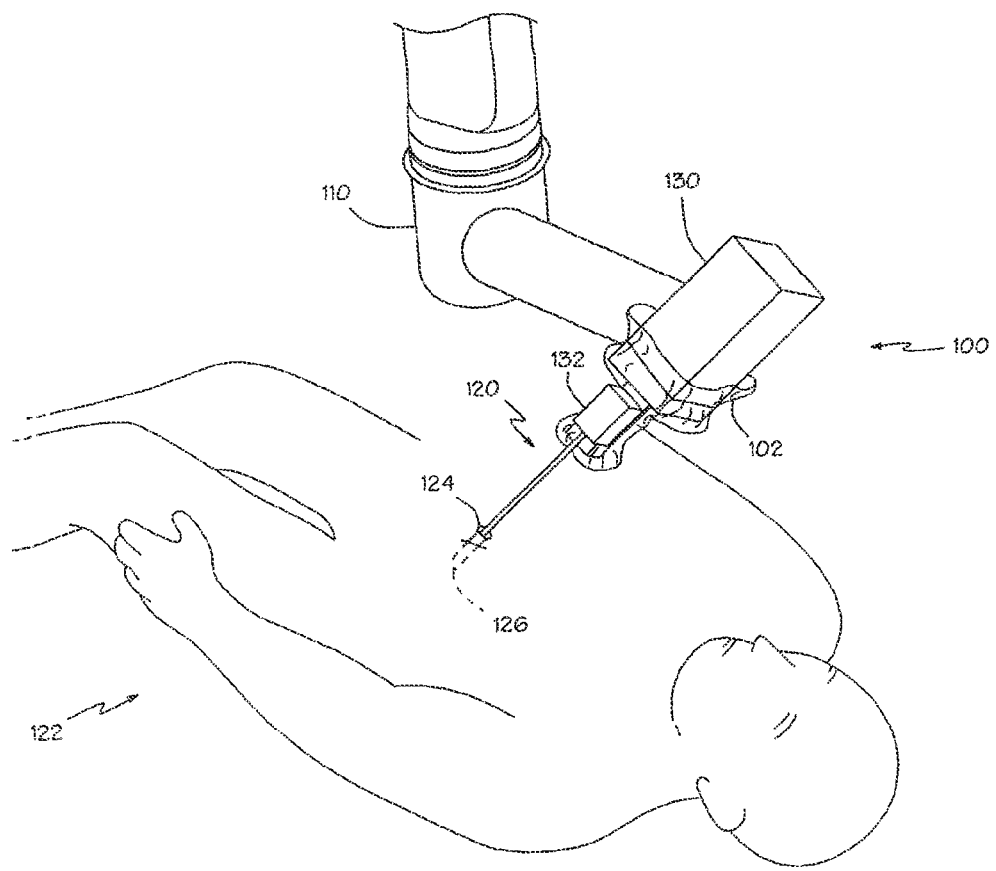
FIG. 1 is a simplified perspective view of a robotic surgical system with a robotically controlled surgical instrument inserted through a port in a patient's abdomen.

FIG. 1 is a simplified perspective view of a robotic surgical system 100, in accordance with embodiments of the present invention. The robotic surgical system 100 shown includes a support assembly 110 mounted to or near an operating table supporting a patient's body. The support assembly 110 enables the delivery of one or more surgical instruments 120 to a surgical site within the patient's body.

The term "instrument" is used herein to describe a device configured to be inserted into a patient's body and used to carry out surgical procedures. The instrument may comprise a single surgical tool, such as a needle driver, a cautery device, or a cutting tool, an imaging device (e.g., an endoscope or ultrasound probe), or a combined device that includes a combination of two or more various tools and imaging devices.

The simplified perspective view of the system 100 shows only a single robotic manipulator 130 supporting a single instrument 120 to allow aspects of the invention to be more clearly seen. A functional robotic surgical system would further include a vision system that enables the operator to view the surgical site from outside the patient's body. The vision system may comprise, e.g., a video monitor displaying images received by an optical device provided at a distal end of one of the surgical instruments 120. The optical device may comprise, e.g., a lens coupled to an optical fiber which carries the detected images to an imaging sensor (e.g., a CCD or CMOs sensor) outside of the patient's body. Alternatively, the imaging sensor may be provided at the distal end of the surgical instrument 120, and the signals produced by the sensor are transmitted along a lead or wirelessly for display on the monitor. An illustrative monitor is the stereoscopic display on the surgeon's cart in the da Vinci® Surgical System, manufactured by Intuitive Surgical, Inc., of Sunnyvale Calif.

A functional robotic surgical system would further include a control system for controlling the insertion and articulation of the surgical assembly 110 and surgical instruments 120. This control may be effectuated in a variety of ways, depending on the degree of control desired, the size of the surgical assembly 110, and other factors. In some embodiments, the control system may include one or more anually operated input devices, such as a joystick, exoskeletal glove, or the like. These input devices control servo motors which, in turn, control the articulation of the surgical assembly 110. The forces generated by the servo motors are transferred via drivetrain mechanisms, which transmit the forces from the servo motors generated outside the patient's body through an intermediate portion of the elongate surgical instrument 120 to a portion of the surgical instrument inside the patient's body distal from the servo motor. The drivetrain mechanism may comprise, e.g., cables in tension, or rods or tubes in compression or under torsion. Persons familiar with telemanipulative surgery will know of systems such as the da Vinci® Surgical System and the Zeus® system originally manufactured by Computer Motion, Inc. and various illustrative components of such systems.

FIG. 1 shows a sterile surgical field 122 in which surgical instrument 120 inserted through an entry guide cannula 124, e.g., a single port in the patient's abdomen. A functional robotic surgical system would provide an entry guide manipulator and an instrument manipulator. The entry guide 124 is mounted onto the entry guide manipulator, which includes a robotic positioning system for positioning the distal end 126 of the entry guide 124 at the desired target surgical site. The robotic positioning system may be provided in a variety of forms, such as, e.g., a serial link arm having multiple degrees of freedom (e.g., six degrees of freedom) or a remote center arm which is positioned by a setup joint mounted onto a base. Alternatively, the entry guide manipulator may be manually maneuvered so as to position the entry guide 124 in the desired location. In some telesurgical embodiments, the input devices that control the manipulator(s) may be provided at a location remote from the patient (outside the room in which the patient is placed). The input signals from the input devices are then transmitted to the control system, which, in turn, manipulates the manipulators 130 in response to those signals. The instrument manipulator is coupled to the entry guide manipulator such that the instrument manipulator 130 moves in conjunction with the entry guide 124.

Embodiments of the invention provide a three component surgical system 100 that includes the robotic manipulator 130, the sterile surgical instrument 120, and the intermediate sterile drape 102 that includes mechanical elements for coupling the robotic manipulator to the surgical instrument and for transferring motion therebetween. The robotic manipulator 130 is thereby shielded from the sterile surgical field 122. The surgical instrument 120 will generally be sterile, often being sterilizable and/or being provided in hermetically sealed packages for use or it may be disposable. The sterile drape 102 is disposable. In contrast, the complex servo mechanism of the robotic manipulator 130 may be difficult and/or impossible to fully sterilize between procedures. Instead, the sterile drape 102 will cover at least a portion of the manipulator to maintain the sterile environment around the patient. In this manner, the robotic manipulator 130 can be draped prior to a surgical procedure to provide a sterile surgical site 122 without damaging the motors or electrical connections within the robotic manipulator in a sterilization procedure.

The sterile drape 102 covers at least a portion of the manipulator. While the sterile drape 102 in FIG. 1 is shown covering only a small portion of the robotic manipulator 130 for clarity, it will be understood that the sterile drape may cover a larger portion or all of the robotic manipulator and even its supporting structure. In other embodiments, the sterile drape may cooperate with additional sterile drapes to cover the robotic manipulator. In other embodiments, the sterile drape may cover more than one robotic manipulator and include multiple mechanical elements for coupling the robotic manipulators to multiple surgical instruments.

The surgical instrument 120 is detachably connected to the robotic manipulator 130. The robotic manipulator includes a coupler 132 to transfer controller motion from the robotic manipulator to the surgical instrument 120. The surgical instrument 120 has a proximal interface 132 and distal end effector. The distal end effector has a plurality of degrees of motion relative to the proximal interface. The degrees of motion are coupled to drive elements of the interface. is disposed adjacent The sterile drape includes a sterile barrier interposed between the manipulator 130 and the interface 132. The sterile barrier includes a first surface driven by the drive elements of the manipulator 130, and a second surface driving the driven elements of the instrument 120.

Figure 2:
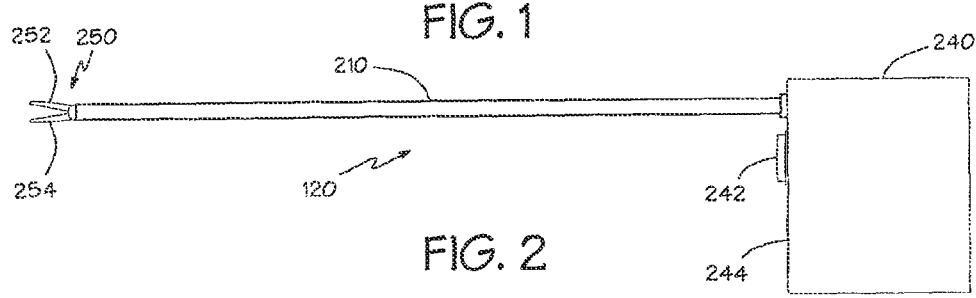
FIG. 2 is a plan view of a surgical instrument for use with a robotic manipulator.

FIG. 2 is a plan view of an illustrative embodiment of the surgical instrument 120, comprising an elongate body portion tube 210, a distal portion 250, and a proximal control mechanism 240. The distal portion 250 of the surgical instrument 120 may provide any of a variety of surgical devices such as the forceps shown, a needle driver, a cautery device, a cutting tool, an imaging device (e.g., an endoscope or ultrasound probe), or a combined device that includes a combination of two or more various tools and imaging devices.

Figures 3, 4:
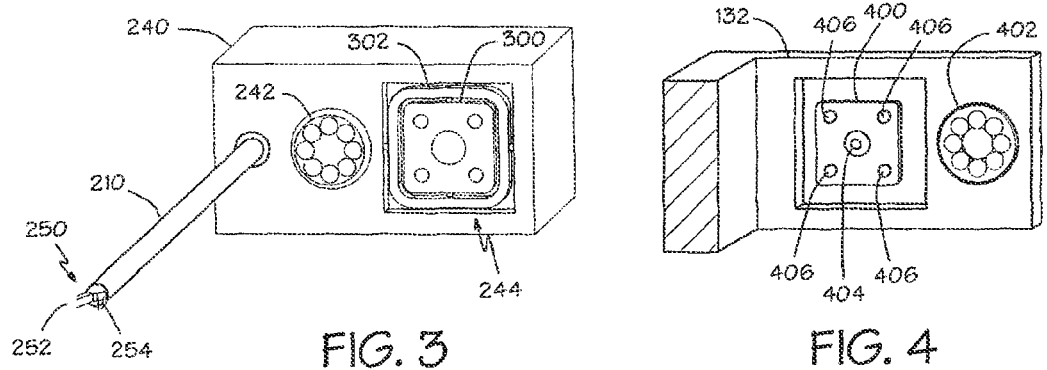
FIG. 3 is a perspective view of the surgical instrument shown in FIG. 2.
FIG. 4 is a perspective view of a coupler portion of a robotic manipulator.

FIG. 3 is a perspective view showing the proximal control mechanism 240 of the surgical instrument 120 in more detail. In this embodiment, a gimbal assembly 244 and a rotary input 242 are provided to receive controlling inputs. The gimbal assembly 244 includes an outer gimbal 302 that is pivotally supported by a housing of the proximal control mechanism 240 and an inner gimbal 300 that is pivotally supported by the outer gimbal. The axes of the inner and outer gimbals intersect and allow the inner gimbal to move with two degrees of rotational freedom, one for each of the two axes of the gimbal assembly.

The two degrees of freedom may control two related motions of the surgical tool 250 provided at the distal portion of the surgical instrument 120 or they may control two unrelated motions. For example, rotation of one axis of the gimbal assembly 244 may control the angular position of one of the forceps jaws 252 and rotation of the other axis may control the angular position of the other jaw 254. In another example, rotation of one axis of the gimbal assembly 244 may open and close the forceps jaws 252, 254 and rotation of the other axis may rotate the forceps 250. In other embodiments, more than one gimbal assembly may be provided to control a greater number of movements of the tool provided at the distal portion of the surgical instrument. The additional gimbal assemblies may be adjacent one another or may be provided on other surfaces of the proximal control mechanism 240 of the surgical instrument 120. The rotary input 242 may rotate the tube 210 or it may control another motion of the surgical instrument 120.

FIG. 4 shows a perspective view of the coupler portion 132 of the robotic manipulator 130. The coupler 132 includes a plate 400 that bears against the inner gimbal 300 of the gimbal assembly 244 in the proximal control mechanism 240 of the surgical instrument 120 when the instrument is connected to the robotic manipulator 130. A pin pivotally supports the plate 400 at a point that coincides with the intersection of the instrument's gimbal axes when the instrument 120 is connected to the manipulator 130. Thus the plate 400 and the inner gimbal 300 of the gimbal assembly 244 rotate with two degrees of freedom about a common center of motion and there is no relative motion between the plate and the inner gimbal. The coupler 132 may further include a rotary output 402 that engages the rotary input 242 of the surgical instrument 120.

Figure 5:
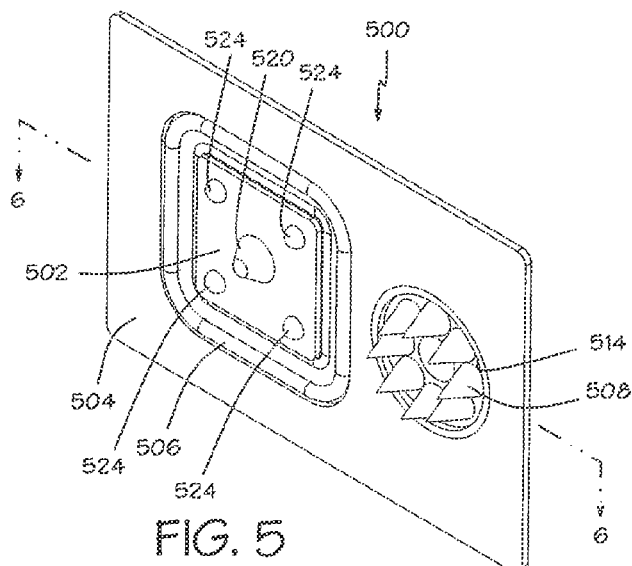
FIG. 5 is a perspective view of a sterile barrier that embodies the invention.
Figure 6:
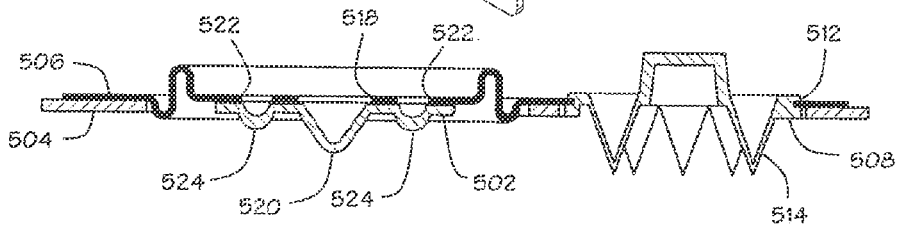
FIG. 6 is a cross-section of the sterile barrier.
Figure 7:
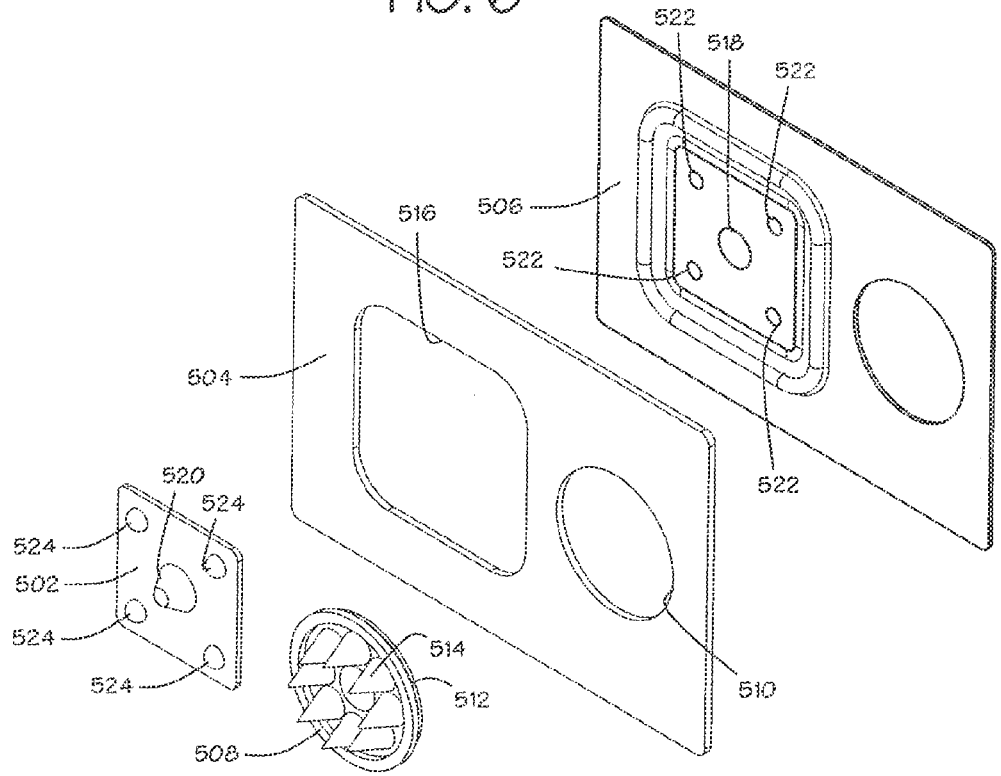
FIG. 7 is a an exploded view of the sterile barrier.
Figure 8:
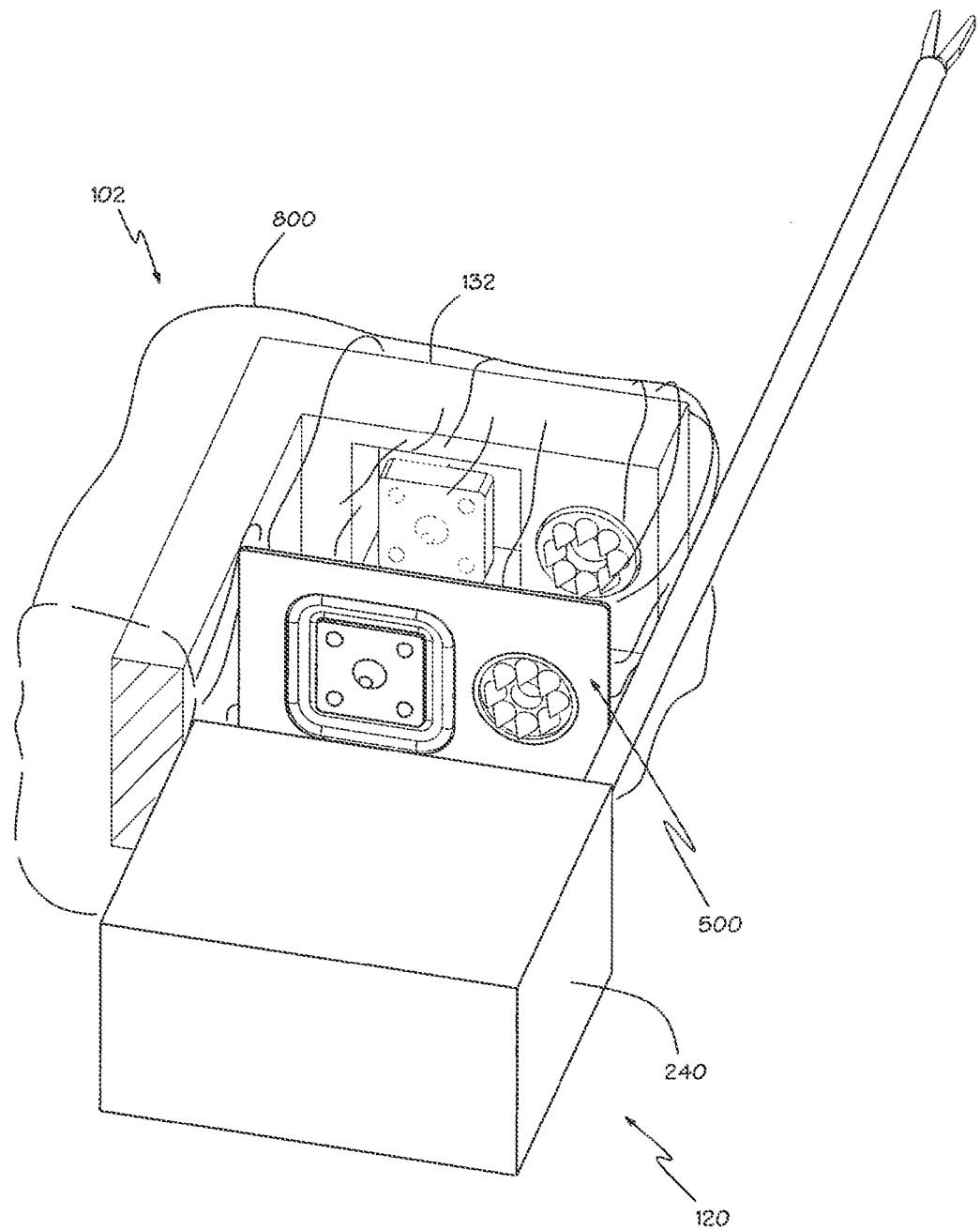
FIG. 8 is a perspective view of the coupler portion of the robotic manipulator showing the sterile drape and the surgical instrument in an exploded configuration that illustrates how the three components relate to one another.

FIG. 5 shows a perspective view of a sterile barrier 500 that may be bonded to a sterile sheet to form a sterile drape that embodies the invention. FIG. 6 is a cross-section of the sterile barrier 500 along section line 6-6. FIG. 7 is an exploded view of the sterile barrier 500. FIG. 8 shows a perspective view of the coupler portion 132 of the robotic manipulator showing the sterile drape 102 and the surgical instrument 120 in an exploded configuration that illustrates how the three components relate to one another. When the surgical instrument 120 is operatively connected to the robotic manipulator 130, the sterile barrier 500 will be closely held between the manipulator and the instrument.

The sterile drape 102 includes a sterile sheet 800 to cover at least a portion of the robotic surgical manipulator. A substantially rigid frame 504 is bonded to the sterile sheet. The frame 504 may be made of polycarbonate, high density polyethylene (HDPE), or other similar material that will provide a stable frame for the sterile barrier 500. The sterile sheet 800 may be made of very thin sheets, on the order of 0.008" or less in thickness, of polyethylene, Ethylene-Methyl-Acrylate (EMA), or other sheet material that provides a pliable, sterilizable barrier that is resistant to punctures or tearing.

An instrument interface 502 is provided to cover the drive plate 400 of the robotic surgical manipulator 130 and transmit the motion of the plate to the inner gimbal 300 of the instrument 120. A diaphragm 506 connects the instrument interface 502 to the frame 504. The diaphragm 506 provides a barrier between the manipulator 130 and the instrument 120. The diaphragm 506 may be convoluted in the region between the instrument interface 502 and the frame 504 to allow the plate 400 to move within an opening 516 in the frame 504. The convoluted diaphragm 506 may be made from an elastomeric material that allows the convolutions to be deformed as required by the motion of the instrument interface 502 and then return to their resting configuration. In other embodiments, the diaphragm may be made from a flat elastomeric material that allows the diaphragm to stretch as required by the motion of the instrument interface and then return to its resting configuration. In other embodiments, the diaphragm may be made from a flat plastic material that allows the diaphragm to be deformed as required by the motion of the instrument interface and thus form convolutions through use.

The diaphragm 506 may further include an opening 518 that receives a protruding portion 404 of the drive plate 400 that extends outwardly from the driving surface to provide the center of motion of the drive plate. The instrument interface 502 may be shaped 520 to receive the protruding portion 404 of the drive plate 400.

The diaphragm 506 may further include a plurality of openings 522 that receive a plurality of alignment features 406 on the driving surface of the drive plate 400 and the instrument interface 502 is shaped 524 to receive the plurality of alignment features.

The frame may further include a coupling 508 disposed in a circular opening 510 adjacent the instrument interface to couple a rotational motion of the rotary driver 402 to the rotary input 242 of the surgical instrument 120. The coupling 508 may include a peripheral groove 512 that engages the diaphragm 506 to provide a seal that allows the coupling to rotate. The coupling may include a face with pointed projections 514 to engage the rotary input 242 of the surgical instrument 120. The projections may be sized and shaped so that the projections tend to enter the mating part and move it into alignment as the instrument 120 is attached to the manipulator 130. The instrument interface 502 and the coupling 508 may be made of polycarbonate, high density polyethylene (HDPE), or other similar materials that have a low compressibility so that they can transmit forces in compression.

Figure 9:
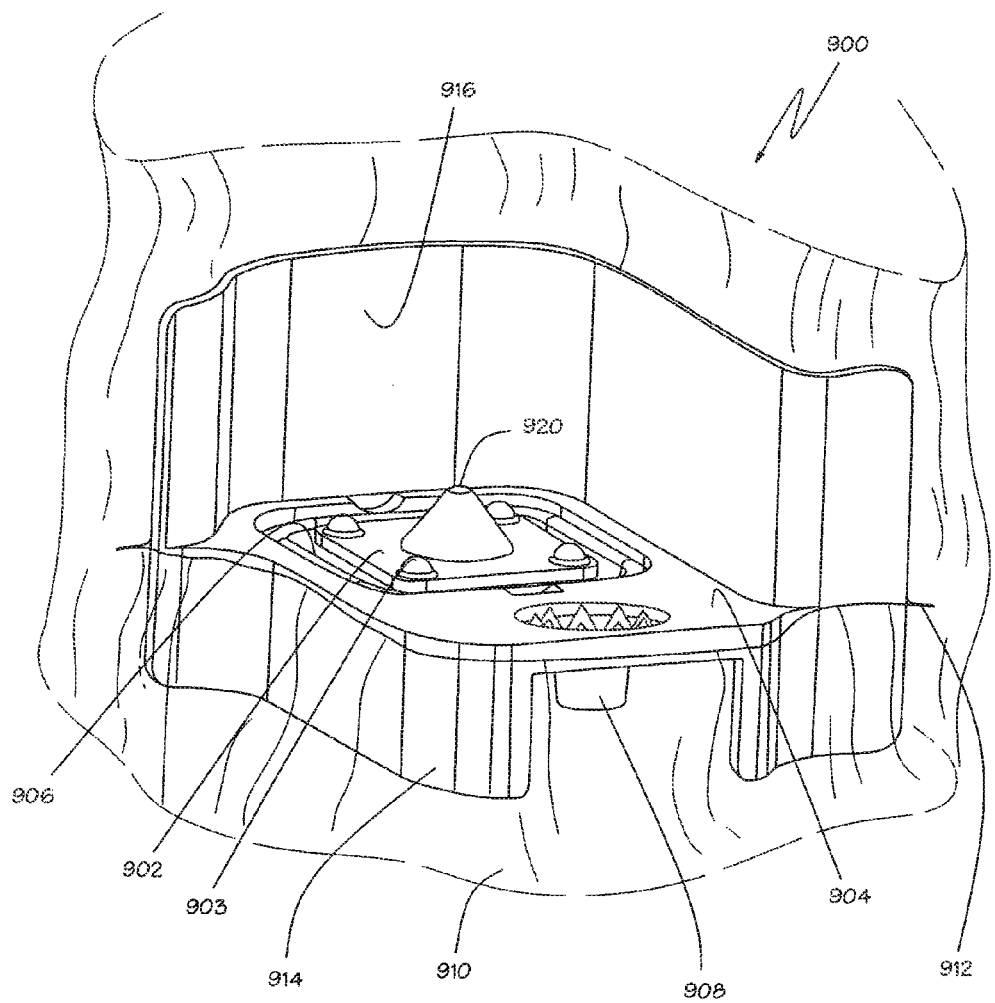
FIG. 9 is a perspective view of another sterile drape that embodies the invention.

FIG. 9 shows a perspective view of another sterile drape 900 that embodies the invention. As in the previously described embodiment, an instrument interface 902 is connected to a substantially rigid frame 904 by a diaphragm 906. The frame 904 further includes an attachment structure 914, 916 to which a sterile sheet 910 is bonded. The attachment structure extends substantially perpendicular to the plane of the diaphragm 906. The attachment structure 914, 916 may allow the frame to be inserted into a single straight slit 912 in the sterile sheet 910 and attached to the sheet.

As in the previously described embodiment, a coupler 908 may be provided to couple rotary motion from the manipulator to the instrument. The instrument interface 902 may be shaped to provide a protruding portion 920 that receives the portion of the manipulator's drive plate that provides the center of motion for the plate.

Figure 10:
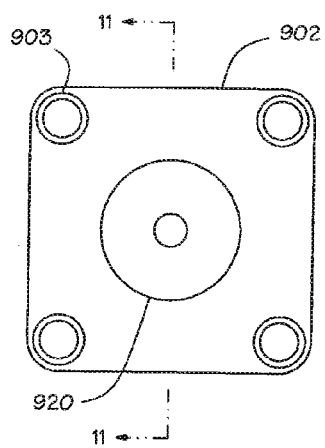
FIG. 10 is a plan view of the instrument interface shown in FIG. 9.
Figure 11:
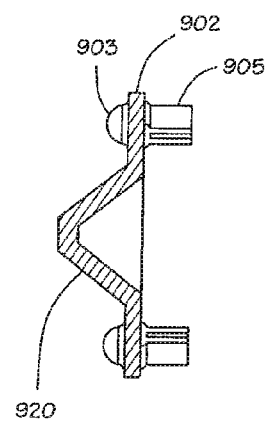
FIG. 11 is a cross section of the instrument interface of FIG. 10 taken along line 11-11.
Figure 12:
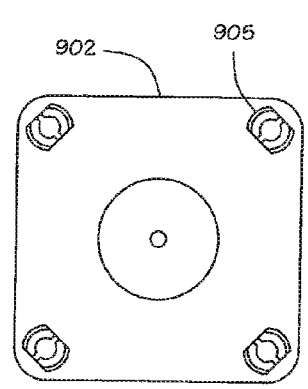
FIG. 12 is a bottom view of the instrument interface of FIG. 10.

FIG. 10 is a plan view of the instrument interface 902. FIG. 11 is a section view taken along section line 11-11. FIG. 12 is a bottom view of the instrument interface 902. As best seen in FIGS. 11 and 12, the instrument interface 902 may include alignment features 905 in the form of cylinders. The cylinders 905 may be received by corresponding holes in the manipulator's drive plate. The cylinders 905 may include a slit to provide a "spring fit" that holds the instrument interface 902 on the drive plate. The sides of the cylinders 905 may be relieved to allow for some mismatch in the spacing of the cylinders and the corresponding holes in the manipulator's drive plate.

While certain exemplary embodiments have been described and shown in the accompanying drawings, it is to be understood that such embodiments are merely illustrative of and not restrictive on the broad invention, and that this invention is not limited to the specific constructions and arrangements shown and described, since various other modifications may occur to those of ordinary skill in the art. The description is thus to be regarded as illustrative instead of limiting.

What is claimed is:

1. A surgical apparatus comprising:
   a sterile sheet that covers at least a portion of a robotic surgical manipulator;
   a substantially rigid frame coupled to the sterile sheet;
   an instrument interface; and
   a diaphragm that connects the instrument interface to the frame, the diaphragm allowing the instrument interface to move with two degrees of rotational freedom when the instrument interface is positioned at least in part between a drive plate of the robotic surgical manipulator and a gimbal assembly of a surgical instrument attached to the robotic surgical manipulator.

2. The surgical apparatus of claim 1 wherein the frame comprises an attachment structure, the attachment structure extending substantially perpendicular to a plane of the diaphragm.

3. The surgical apparatus of claim 1 further comprising a coupling adjacent the instrument interface, the coupling rotating when the coupling is at least in part between a rotary output of the robotic surgical manipulator and a rotary input of the surgical instrument attached to the robotic surgical manipulator.

4. The surgical apparatus of claim 3 wherein the coupling comprises a peripheral groove that engages the diagram to provide a seal that allows the coupling to rotate.

5. The surgical apparatus of claim 3 wherein the coupling includes a face with projections to engage the surgical instrument.

6. The surgical apparatus of claim 1 wherein the instrument interface transmits motion of the drive plate to the gimbal assembly.

7. The surgical apparatus of claim 1 wherein the diaphragm and the instrument interface are configured to receive a protruding portion of the drive plate that extends outwardly from a driving surface and beyond the center of motion of the drive plate.

8. The surgical apparatus of claim 1 wherein the diaphragm comprises a plurality of openings that receive a plurality of alignment features on the drive plate.

9. The surgical apparatus of claim 1 wherein the diaphragm is convoluted in a region between the instrument interface and the frame.

10. The surgical apparatus of claim 1 further comprising the robotic surgical manipulator, and the surgical instrument coupled to the robotic surgical manipulator.

11. A method comprising:
    covering a robotic surgical manipulator at least in part by a sterile sheet that comprises a substantially rigid frame; and
    positioning an instrument interface at least in part between a drive plate of the robotic surgical manipulator and a two degree of freedom gimbal assembly of a surgical instrument coupled to the robotic surgical manipulator, the instrument interface being connected to the frame by a diaphragm that allows the instrument interface to move with two rotational degrees of freedom.

12. The method of claim 11 further comprising positioning a rotating coupling between a rotary output of the robotic surgical manipulator and a rotary input of the surgical instrument, the coupling being adjacent the instrument interface.

13. The method of claim 12 further comprising establishing a rotational seal between the coupling and the diaphragm.

14. The method of claim 12 further comprising engaging and aligning the coupling and the rotary input of the surgical instrument with projections.

15. The method of claim 12 further comprising engaging and aligning the coupling and the rotary output of the robotic surgical manipulator with projections.

16. The method of claim 11 further comprising transmitting motion of the drive plate to the gimbal assembly through the instrument interface.

17. The method of claim 11 further comprising extending a portion of the drive plate that extends outwardly from a driving surface and beyond the center of motion of the drive plate into openings in the diaphragm and the instrument interface.

18. The method of claim 11 wherein the diaphragm further includes a plurality of openings that receive a plurality of alignment features on the instrument interface.

19. The method of claim 11 wherein the diaphragm is convoluted in a region between the instrument interface and the frame.

* * * * *